United States Patent [19]

Lartey et al.

[11] Patent Number: 5,696,084
[45] Date of Patent: Dec. 9, 1997

[54] AMINO-LIPOPEPTIDE ANTIFUNGAL AGENTS

[75] Inventors: Paul A. Lartey, Wadsworth; Leping Li, Gurnee; Larry Lewis Klein, Lake Forest, all of Ill.; Christina Louise Leone, Kenosha, Wis.; Sheela Albert Thomas, Vernon Hills; Ming Clinton Yeung, Grayslake, both of Ill.; David Allen Degoey, Kenosha, Wis.; David J. Grampovnik, Waukegan, Ill.

[73] Assignee: Abbott Laboratories, Abbott Park, Ill.

[21] Appl. No.: 698,610

[22] Filed: Aug. 16, 1996

[51] Int. Cl.$^6$ .......................... A61K 38/00; A61K 38/12; C07K 5/00
[52] U.S. Cl. ............................................ 514/9; 530/317
[58] Field of Search ................................ 514/9; 530/317

[56] References Cited

U.S. PATENT DOCUMENTS 5,502,033  3/1996  Iwamoto et al. ................. 514/11

FOREIGN PATENT DOCUMENTS

| | | |
|---|---|---|
| 0561639 | 9/1993 | European Pat. Off. |
| 9606109 | 2/1996 | WIPO |
| 9608266 | 3/1996 | WIPO |
| 9608267 | 3/1996 | WIPO |
| 9611210 | 4/1996 | WIPO |

OTHER PUBLICATIONS

Zambias, R. A., et al., "Preparation and Structure–Activity Relationships of Simplified Analogues of the Antifungal Agent Cilofungin: A Total Synthesis Approach", J. Med. Chem., vol. 35, No. 15, 1992, pp. 2843–2855.

Kurokawa, N., et al., "Total Synthesis of Echinocandins. 1. Sterocontrolled Syntheses of the Constituent Amino Acids", J. Am. Chem. Soc., 108, No. 19, 1986, pp.6041–6045.

Balkovec, J. M., "Lipopeptide antifungal agents", Section Review–Anti–infectives, Expert. Opin. Invest. Drugs, (1994) 3(2), pp. 65–82.

Primary Examiner—Douglas W. Robinson
Assistant Examiner—Kent L. Bell
Attorney, Agent, or Firm—Mona Anand

[57] ABSTRACT

Disclosed are novel antifungal agents having the formula:

or a pharmaceutically acceptable acid, ester or prodrug thereof, wherein preferred compounds include those compounds wherein $R_1$ is selected from the group consisting of $-NH_2$; $R_2$ is selected from the group consisting of hydrogen, fluoro, and hydroxyl; $R_3$ is selected from the group consisting of $-CH_2(p-C_6H_4)_3O(CH_2)_3CH_3$, $-CH_2(p-C_6H_4)O(CH_2)_6CH_3$, $-COO(p-C_6H_4)O(CH_2)_6CH_3$, $-CO(Piperazinyl)(p-C_6H_4)_2OCH_3$, $-CO(p-C_6H_4)O(CH_2)_6CH_3$, $-CO(p-C_6H_4)(Piperazinyl)(p-C_6H_4)O(CH_2)_4CH_3$, $-CO(p-C_6H_4)(Piperazinyl)(p-C_6H_4)O(CH_2)_6CH_3$, $-CO(p-C_6H_4)(Piperazinyl)(p-C_6H_4)OCH_3$, and $-CO(p-C_6H_4)(Piperazinyl)O(CH_2)_6CH_3$; and $R_4$ is selected from the group consisting of $-CH(OH)CH_3$, $-CH_2OH$, $-CH_2CH_3$, $-CH_2CH_2CH_2NH_2$, $-CH_2(CH_2)NH_2$, $-CH_2NH_2$, $-CH_2(CH_2)_2(NH)C=(NH)-NH_2$, $-CH_3$, $-CH_2(Ph)OH$, hydrogen, $-CH_2CH_2COOH$, and $-CH_2COOH$. Also disclosed are pharmaceutical compositions containing such compounds and the use of the same in the treatment of fungal infections.

16 Claims, No Drawings

AMINO-LIPOPETIDE ANTIFUNGAL AGENTS

TECHNICAL FIELD

The present invention relates to novel cyclic hexapeptide derivatives having antifungal activity, as well as to methods useful for their preparation, pharmaceutical compositions containing such compounds, and a method of treating fungal infections.

BACKGROUND OF THE INVENTION

The echinocandins are a well known class of cyclic peptides characterized by their antifungal activity against various fungi especially *Candida albicans* species and are described in *Helv. Chim. Acta*, 57, 2459–2477 (1974). The echinocandins along with other similar isolates such as pneumocandin, mulundocandin and aculeacin all inhibit a key fungal enzyme, β-1,3-glucan synthase. This enzyme produces glucan which is an integral component of the fungal cell wall. It has been shown that inhibition of the production of glucan leads to loss of the fungal cell wall integrity and subsequent cell death. Since this enzyme is not present in mammals, it constitutes a selective and essential target for antifungal agents.

Traditionally, echinocandins were isolated from a strain of *Aspergillus ruglos* and *Aspergillus nidulans*. Recent efforts towards synthesizing these cyclic polypeptides have resulted in semi-synthetic echinocandins which are disclosed in EP 561,639 A1, published Sep. 22, 1993 and analogs disclosed in WO 96/08266 published Mar. 21, 1996, WO 96/08267, published Mar. 21, 1996 and WO 96/06109 published Feb. 29, 1996. WO 96/11210 published Apr. 18, 1996 discloses cyclic hexapeptides having antibiotic activity.

Total synthesis of echinocandin D in solution phase was first described in *J. Am. Chem. Soc.*, 108, 6041–6043 (1986). More recently, total synthesis of some of other related compounds known as cilofungins via solid phase synthesis has been undertaken and is described in *J. Med. Chem.*, 35, 2843–2855 (1992). The study was undertaken to understand the structure-activity relationships of the peptide portion of the system. The results suggest that the L-homotyrosine residue found in echinocandin-type ring system is a crucial structural element for good β-1,3-glucan synthesis inhibition and Candida antifungal activity.

However, there is a need for discovering new hexapeptide nuclei which would exhibit enhanced water solubility suitable for parental administration, increased stability of the peptide nucleus and retain excellent whole cell antifungal activity against a variety of *Candida albicans* strains. The use of total synthesis to prepare these nuclei, therefore, allows for maximal introduction of amine functionalities which would not otherwise be available through fermentation and isolation techniques.

SUMMARY OF THE INVENTION

It has now been discovered that the cyclic hexapeptides of the invention prepared by total synthesis exhibit excellent whole cell antifungal activity and improved water solubility while also providing new sites for further chemical modification.

In one aspect, therefore, the present invention relates to new cyclic hexapeptides represented by formula I

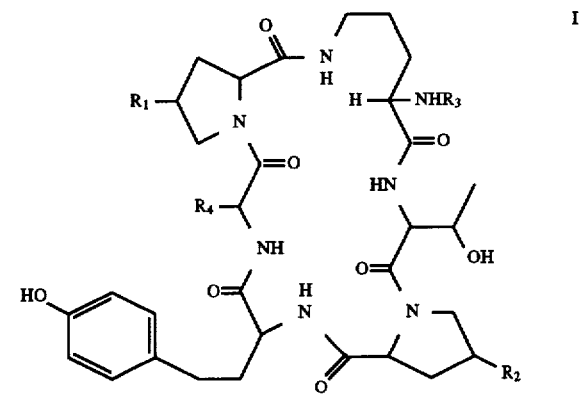

or a pharmaceutically acceptable acid, ester or prodrug thereof, wherein $R_1$ is $NR_5R_6$;

$R_2$ is selected from the group consisting of hydrogen, hydroxyl, halo, and amino;

$R_3$ is selected from the group consisting of —$COR_7$, —$COOR_7$, or —$CH_2R_7$;

$R_4$ is selected from the group consisting of hydrogen, alkyl, hydroxyalkyl, aminoalkyl, di- and trialkylaminoalkyl, p-hydroxyaryl(alkyl), guanidinoalkyl, carboxyalkyl, arylalkyl and heteroarylalkyl;

$R_5$ and $R_6$ are independently at each occurrence selected from the group consisting of hydrogen, lower alkyl, arylalkyl, aminoalkyl, hydroxy(amino alkyl), carboxyalkyl, di- and trialkylaminoalkyl, guanidinyl, and —$COR_8$, or taken together with atoms to which each is attached, $R_5$ and $R_6$ form a 5- or 6- membered ring containing one nitrogen atom;

$R_7$ is selected from the group consisting of aryl, aryl-aryl, aryl-aryl-aryl, arylalkyl, alkylaryl, arylalkoxy, aryl-heteroaryl, hetero-aryl-aryl, aryl-aryl-hetero, and aryl-heteroalkyl; and $R_8$ is selected from the group consisting of lower alkyl, mono-, di- and trialkylaminoalkyl, hydroxy(aminoalkyl), carboxyalkyl, hetero(alkylamino alkyl), hydrazinyl, alkenyloxy, heterocyclic, heteroaromatic, alkoxy, aryl, and arylalkyl.

In another aspect, the present invention relates to pharmaceutical compositions which comprise a compound of the invention in combination with a pharmaceutically acceptable carrier.

In still another aspect, the present invention relates to a method of treating human or veterinary patient comprising administering to a patient a therapeutically effective amount of a compound of the invention.

DETAILED DESCRIPTION OF THE INVENTION

Definitions

As used throughout this specification and in the appended claims, the following terms have the meanings specified:

The terms "loweralkyl" or "alkyl" as used herein refer to straight or branched chain alkyl radicals containing from 1 to 20 carbon atoms, sometimes represented as Cx-Cy-alkyl where x and y respectively represent the minimum and maximum number of carbon atoms in the alkyl radical. Examples of loweralkyl include, but are not limited to, methyl, ethyl, n-propyl, isopropyl, n-butyl, isobutyl, sec-butyl, t-butyl, n-pentyl, 1-methylbutyl, 2,2-dimethylbutyl, 2-methylpentyl, 2,2-dimethylpropyl, n-hexyl and the like.

The term "aminoalkyl" as used herein refers to lower alkyl groups, as defined above, substituted with from one or more amino groups, respectively, such as N,N-dimethylaminoethyl, aminopropyl and the like.

The term "alkylamino" as used herein refers to amino group substituted with a loweralkyl group, for example, ethylamino, butylamino, and the like.

The term "di- and trialkylamino" as used herein refers to an amino groups which is substituted, respectively, with two or three lower alkyl group as defined above, for example diethylamino, methyl propylamino, and the like.

The term "alkoxy" or "lower alkoxy" as used herein refers to a loweralkyl group, as defined above, which is bonded to an oxygen atom in an ether linkage. Examples of alkoxy include, but are not limited to, methoxy, ethoxy, isopropoxy, n-pentyloxy, t-butoxyl n-octoyloxy and the like. This alkoxy radical can also contain a ring which include, but are not limited to, five or six atom ring composed of carbons, one or two heteroatoms such as nitrogen, oxygen, or sulfur.

The term "aryloxy" as used herein refers to an aryl group defined below, which is bonded to the parent molecular moiety through an oxygen atom in an ether linkage. Examples of aryloxy include, but are not limited to, phenoxy, naphthoxy and the like.

The term "alkenyl" as used herein refers to a branched or straight hydrocarbon chain comprising two to twenty carbon atoms, preferably four to twelve carbon atoms, especially about eight to ten carbon atoms, which also comprises one or more carbon-carbon double bonds, preferably about one to three double bonds. Compounds of the invention may either have a known configuration or may exist as a mixture of isomers.

The term "cycloalkyl" as used herein refers to a saturated monocyclic hydrocarbon groups having from three to seven carbon atoms in the ring, including, but not limited to, cyclopropyl cyclobutyl cyclopentyl, cyclohexyl, cycloheptyl and the like. The cyclic group may be optionally substituted with, for example, lower alkyl, hydroxy, halogen or an amino.

The term "alkenyloxy" as used herein refers to a branched or straight hydrocarbon chain comprising two to twelve carbon atoms which also comprises one or more carbon-carbon double bonds which is linked to the parent molecular moiety through an oxygen atom. Representative alkenyloxy groups include 2-propenyloxy (i.e., allyl) and the like.

The term "aryl" as used herein refers to a mono-, fused bicyclic or fused tricyclic carbocyclic ring system having one or more aromatic rings including, but not limited to, phenyl, naphthyl, tetrahydronaphthyl, phenanthrenyl, biphenylenyl, indanyl, indenyl and the like. The term "bicyclic aryl" as used herein includes naphthyl, tetrahydronaphthyl, indanyl, indenyl and the like. The term "tricyclic aryl" as used herein includes anthracenyl, phenanthrenyl, biphenylenyl, fluorenyl, and the like. Aryl groups (including bicyclic and tricyclic aryl groups) can be unsubstituted or substituted with one, two or three substituents independently selected from loweralkyl, haloalkyl, alkoxy, thioalkoxy, amino, alkylamino, dialkylamino, alkenyloxy, hydroxy, halo, mercapto, nitro, carboxaldehyde, carboxy, alkoxycarbonyl and carboxamide. Substituents also include methylenedioxy and ethylenedioxy. In addition, substituted aryl groups include tetrafluorophenyl and pentafluorophenyl.

The term "aryl-aryl-" as used herein refers to two aryl groups which are the same or different linked by a covalent bond. Examples of aryl-aryl- include, but are not limited to, biphenyl, 4-(1-naphthyl)phenyl, 4-(2-naphthyl)phenyl, 4-phenylnaphth-1-yl and the like. The covalent linking bonds in aryl-aryl- are preferably para, i.e., 1,4-; and the preferred aryl-aryl- group is biphenyl. The aryl groups in aryl-aryl are preferably substituted with alkoxy or aryloxy groups in the para position.

The term "aryl-aryl-aryl-" as used herein refers to three aryl groups which are the same or different linked to each other by covalent bonds. Examples of aryl-aryl-aryl- include, but are not limited to, 4-(biphenyl)-phenyl, 4-(biphenyl)naphth-1-yl, 6-(biphenyl)naphth-2-yl and the like. The covalent linking bonds in aryl-aryl-aryl- are preferably para, i.e., 1,4-. These groups are preferably substituted with alkoxy groups in the para position. The preferred aryl-aryl-aryl- group is 4-((4'-alkoxy)biphenyl))phenyl.

The term "aryl-hetero-aryl or hetero-aryl-aryl or aryl-aryl-hetero" as used herein refers to aryl, hetero (as defined below) and aryl groups (as defined above) which are same or different linked to each other by covalent bonds in the designated sequence. These groups are preferably substituted with alkoxy groups in the para position. Examples include, but are not limited to, 4-(4-(4'-alkoxyphenyl) piperazinyl)phenyl, 4-((4'-alkoxy-(biphenyl))piperazinyl, 4'-((4-alkylpiperazinyl))biphenyl, and the like. The covalent linking bond between the groups are preferably para, i.e., in 1,4- position.

The term "arylalkyl" as used herein refers to an aryl group as previously defined, appended to a loweralkyl radical, for example, benzyl and the like.

The term "alkanoyl" as used herein means an alkyl group as defined above, attached to the parent molecular moiety through a carbonyl group. Examples include, but are not limited to, acetyl, propionyl, butanoyl, and the like.

The term "carboxyalkyl" as used herein means a lower alkyl group substituted with a carboxylic group.

The terms "heterocyclic ring" or "heterocyclic" or "heterocycle" as used herein refers to any 3- or 4-membered ring containing a heteroatom selected from oxygen, nitrogen and sulfur; or a 5-, 6- or 7-membered ring containing one, two or three nitrogen atoms; one nitrogen and one sulfur atom; or one nitrogen and one oxygen atom. The 5-membered ring has 0–2 double bonds and the 6- and 7-membered ring have 0–3 double bonds. The nitrogen heteroatoms can be optionally quaternized. The term "heterocyclic" also includes bicyclic groups in which any of the above heterocyclic rings is fused to a benzene ring or a cyclohexane ring or another heterocyclic ring (for example, indolyl, quinolyl, isoquinolyl, tetrahydroquinolyl, decahydroquinolyl, benzofuryl or benzothienyl, imidazopyridyl, pyrrolopyridyl and the like). The term "heterocyclic" also includes tricyclic groups in which any of the above heterocyclic rings is fused to two benzene rings or two cyclohexane rings or two other heterocyclic rings (for example, carbazolyl, iminodibenzyl and the like). Heterocyclics include: azetidinyl, benzimidazolyl, 1,4-benzodioxanyl, 1,3-benzodioxolyl, benzoxazolyl, benzothiazolyl, benzothienyl, carbazolyl, dihydropyranyl, dihydrofuranyl, dioxanyl, dioxolanyl, furyl, homopiperidinyl, imidazolyl, imidazolinyl, imidazolidinyl, imidazopyridyl, iminodibenzyl, indolinyl, indolyl, isoquinolinyl, isothiazolidinyl, isothiazolyl, isoxazolidinyl, isoxazolyl, morpholinyl, naphthyridinyl, oxazolidinyl, oxazolyl, piperazinyl, piperidinyl, pyranyl, pyrazinyl, pyrazolidinyl, pyrazolinyl, pyrazolyl, pyridazinyl, pyridyl, pyrimidinyl, pyrrolidinyl, pyrrolindinylpyridyl, pyrrolinyl, pyrrolopyridyl, pyrrolyl, quinolinyl, tetrahydrofuranyl, tetrahydropyranyl, thiazolidinyl, thiazolyl, and thienyl.

Heterocyclics can be unsubstituted or monosubstituted or disubstituted with substituents independently selected from hydroxy, halo, oxo (=O), alkylimino (R*N=wherein R* is a loweralkyl group), amino, alkylamino, dialkylamino, alkoxy, alkoxyalkoxy, haloalkyl, cycloalkyl, aryl, arylalkyl, —COOH, —SO$_3$H and loweralkyl. In addition, nitrogen containing heterocycles can be N-protected.

The term "(heterocyclic)alkyl" as used herein refers to a heterocyclic group as defined above appended to a loweralkyl radical as defined above.

The term "heteroaromatic" as used herein refers to a heterocyclic as defined above, which has conjugated double bonds in its ring system.

The term "hydrazinyl" as used herein refers to hydrazine which is attached to the parent molecule through one of its nitrogen. The nitrogen atoms in the hydrazine molecule may be further independently substituted with one or more lower alkyl groups.

The term "hydroxyalkyl" as used herein refers to a lower alkyl group as defined above, which is substituted with a hydroxy groups at one or more carbon atoms.

The term "hydroxy(aminoalkyl)" as used herein refers to a lower alkyl group, as defined above, which is substituted with hydroxy and amino groups at different carbon atoms.

The term "hydroxy-protecting group" or "O-protecting group" as used herein refers to a removable substituent which protects hydroxyl groups against undesirable reactions during synthetic procedures such as those O-protecting groups disclosed in T. H. Greene and P. G. M. Wuts, "Protective Groups in Organic Synthesis", 2nd edition, John Wiley & Sons, New York (1991), which is incorporated herein by reference. O-Protecting groups comprise substituted methyl ethers, for example, methoxymethyl, benzyloxymethyl, 2-methoxyethoxymethyl, 2-(trimethylsilyl)ethoxy-methyl, t-butyl, benzyl and triphenylmethyl; tetrahydropyranyl ethers; substituted ethyl ethers, for example, 2,2,2-trichloroethyl; silyl ethers, for example, trimethylsilyl, triethylsilyl, t-butyldimethylsilyl and t-butyl-diphenylsilyl; and esters prepared by reacting the hydroxyl group with a carboxylic acid, for example, acetate, propionate, benzoate and the like.

The term "hydroxy-protecting reagent" as used herein refers to those reagents which react with the hydroxy functionality to give the hydroxy protecting groups described above. For example, the hydroxy-protecting reagent triethylsilyl triflate affords the triethylsilyl hydroxy-protecting group. These reagents are described in Greene and Wuts, "Protective Groups In Organic Synthesis," 2nd edition, John Wiley & Sons, New York (1991).

The term "pharmaceutically acceptable salts, esters, and prodrugs" as used herein refers to those carboxylate salts, esters, and prodrugs of the compound of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. Pharmaceutically acceptable salts are well known in the art and refer to the relatively non-toxic, inorganic and organic acid addition salts of the compound of the present invention. For example, S. M. Berge, et al. describe pharmaceutically acceptable salts in detail in *J. Pharmaceutical Sciences* 66:1–19 (1977) which is incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalene-sulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Examples of pharmaceutically acceptable, non-toxic esters of the compounds of this invention include $C_1$ to $C_6$ alkanoyl esters wherein the alkanoyl group is a straight or branched chain. Esters of the compounds of the present invention may be prepared according to conventional methods.

The term "pharmaceutically acceptable prodrugs" as used herein refers to those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, *Pro-drugs as Novel Delivery Systems*, Vol. 14 of the A.C.S. Symposium Series, and in Edward B. Roche, ed., *Bioreversible Carriers in Drug Design*, American Pharmaceutical Association and Pergamon Press, 1987, both of which are incorporated herein by reference.

Where appropriate, prodrugs of derivatives of compounds of the present invention may be prepared by any suitable method. For those compounds in which the prodrug moiety is an amino acid or peptide functionality, the condensation of the amino group with amino acids and peptides may be effected in accordance with conventional condensation methods such as the azide method, the mixed acid anhydride method, the DCC (dicyclohexyl-carbodiimide) method, the active ester method (p-nitrophenyl ester method, N-hydroxy-succinic acid imide ester method, cyanomethyl ester method and the like), the Woodward reagent K method, the DCC-HOBT (1-hydroxy-benzotriazole) method and the like. Classical methods for amino acid condensation reactions are described in M. Bodansky, Y. S. Klausner and M. A. Ondetti, *Peptide Synthesis*, Second Edition, NY, 1976, which is incorporated herein by reference.

Asymmetric centers may exist in the compounds of the present invention. Cis and trans isomers may also exist in the compounds of the present invention. Except where otherwise noted, the present invention contemplates the various stereoisomers, cis and trans isomers and mixtures thereof.

Preferred compounds of the invention are compounds of Formula I wherein $R_1$ is $NH_2$, or $NR_5R_6$, wherein one of $R_5$ and $R_6$ is selected from the group consisting of hydrogen, lower alkyl and $COR_8$, where $R_8$ is lower alkyl; and the other is selected from the group consisting of lower alkyl, arylalkyl, aminoalkyl, hydroxy(aminoalkyl), carboxyalkyl, di- and trialkylamino-alkyl, guanidinyl, and $—COR_8$, wherein $R_8$ is as defined before.

Preferred compounds of the invention also include the compounds of Formula I, wherein $R_2$ is selected from the group consisting of hydrogen, fluoro, and hydroxyl.

Preferred compounds of the invention also include the compounds of Formula I, wherein $R_3$ is selected from the group consisting of $CO(p-C_6H_4)_3O(CH_2)_4CH_3$, $—CH_2(p-C_6H_4)_3O(CH_2)_4CH_3$, $—CH_2p-C_6H_4O(CH_2)_7CH_3$, $—COO(p-C_6H_4)O(CH_2)_7CH_3$, $—CO(p-C_6H_4)O(CH_2)_7CH_3$, $—CO(p-C_6H_4)-(Piperazinyl)(p-C_6H_4)O(CH_2)_4CH_3$, $—CO(p-C_6H_4)(Piperazinyl)(p-C_6H_4)—O(CH_2)_7CH_3$, and $—CO(p-C_6H_4)(Piperazinyl)O(CH_2)_7CH_3$.

Other preferred compounds of the invention are those represented by Formula I, wherein $R_4$ is selected from the group consisting of $—CH(OH)CH_3$, $—CH_2OH$, $—CH_2CH_3$, $—(CH_2)_nCH_2NH_2$, $(CH_2)_nCH_2(NH)C=(NH)NH_2$, $—CH_3$, $—CH_2(C_6H_5)OH$, hydrogen, $—CH_2CH_2COOH$, and $—CH_2COOH$, wherein n is from 0 to 5.

More preferred compounds are those represented by Formula I, wherein $R_1$ is $—NH_2$, $R_2$ is hydroxyl, $R_3$ is $—(p-C_6H_4)_3O(CH_2)_4CH_3$, or $—(p-C_6H_4)(Piperazinyl)(p-C_6H_4)O(CH_2)_7CH_3$, and $R_4$ is $—CH(OH)CH_3$, $—CH_2OH$, $—CH_2CH_2CH_2NH_2$, or $—CH_2NH_2$.

Representative of the preferred compounds of the invention include, but are not limited to the following compounds of Formula I, wherein $R_1$ is $—NH_2$, $R_2$ is $—OH$, $R_3$ is $—CO(p-C_6H_4)_3O(CH_2)_4CH_3$, and $R_4$ is $—CH_2OH$;

$R_1$ is $—NH_2$, $R_2$ is $—OH$, $R_3$ is $—CO(p-C_6H_4)_3O(CH2)_4CH_3$, and $R_4$ is $—CH(OH)CH3$;

$R_1$ is $—NH_2$, $R_2$ is $—OH$, $R_3$ is $—CO(p-C_6H_4)_3O(CH_2)_4CH_3$, and $R_4$ is $—CH_2CH_3$;

$R_1$ is $—NH_2$, $R_2$ is $—OH$, $R_3$ is $—CO(p-C_6H_4)_3O(CH_2)_4CH_3$, and $R_4$ is $—CH_2CH_2CH_2NH_2$;

$R_1$ is $—NH_2$, $R_2$ is $—OH$, $R_3$ is $—CO(p-C_6H_4)_3O(CH_2)_4CH_3$, and $R_4$ is $—CH_2(CH_2)_3NH_2$;

$R_1$ is $—NH_2$, $R_2$ is $—OH$, $R_3$ is $—CO(p-C_6H_4)_3O(CH_2)_4CH_3$, and $R_4$ is $—CH_2NH_2$;

$R_1$ is $—NH2$, $R_2$ is $—OH$, $R_3$ is $—CO(p-C_6H_4)_3O(CH_2)_4CH_3$, and $R_4$ is -2-(p-hydroxyphenyl)ethyl;

$R_1$ is $—NH_2$, $R_2$ is $—OH$, $R_3$ is $—CO(p-C_6H_4)_3O(CH_2)_4CH_3$, and $R_4$ is -3-guanidinopropyl;

$R_1$ is $—NH_2$, $R_2$ is $—OH$, $R_3$ is $—CO(p-C_6H_4)_3O(CH_2)_4CH_3$, and $R_4$ is $—H$;

$R_1$ is $—NH_2$, $R_2$ is $—F$, $R_3$ is $—CO(p-C_6H_4)_3O(CH_2)_4CH_3$, and $R_4$ is $—CH(OH)CH_3$;

$R_1$ is $—NHCH_3$, $R_2$ is $—OH$, $R_3$ is $CO(p-C_6H_4)_3O(CH_2)_4CH_3$, and $R_4$ is $—CH(OH)CH_3$;

$R_1$ is $—N(CH_3)_2$, $R_2$ is $—OH$, $R_3$ is $CO(p-C_6H_4)_3O(CH_2)_4CH_3$, and $R_4$ is $—CH(OH)CH_3$;

$R_1$ is $—NHCH_2(C_6H_5)$, $R_2$ is $—OH$, $R_3$ is $CO(p-C_6H_4)_3O(CH_2)_4CH_3$, and $R_4$ is $—CH(OH)CH_3$;

$R_1$ is $—NHCH_2p-(C_6H_4)OCH_2COOH$, $R_2$ is $—OH$, $R_3$ is $CO(p-C_6H_4)_3O—(CH_2)_4CH_3$, and $R_4$ is $—CH(OH)CH_3$;

$R_1$ is $—NHCH_2(4-Pyridinyl)$ $R_2$ is $—OH$, $R_3$ is $CO(p-C_6H_4)_3O(CH_2)_4CH_3$, and $R_4$ is $—CH(OH)CH_3$;

$R_1$ is $—NHCH_2COOH$, $R_2$ is $—OH$, $R_3$ is $CO(p-C_6H_4)_3O(CH_2)_4CH_3$, and $R_4$ is $—CH(OH)CH_3$;

$R_1$ is $—NHCOCH_2CH_3$, $R_2$ is $—OH$, $R_3$ is $CO(p-C_6H_4)_3O(CH_2)_4CH_3$, and $R_4$ is $—CH(OH)CH_3$;

$R_1$ is $—NHCOCH_3$, $R_2$ is $—OH$, $R_3$ is $CO(p-C_6H_4)_3O(CH_2)_4CH_3$, and $R_4$ is $—CH(OH)CH_3$;

$R_1$ is $—NHCOC_6H_5$, $R_2$ is $—OH$, $R_3$ is $CO(p-C_6H_4)_3O(CH_2)_4CH_3$, and $R_4$ is $—CH(OH)CH_3$;

$R_1$ is $—NHCO(2-furoyl)$, $R_2$ is $—OH$, $R_3$ is $CO(p-C_6H_4)_3O(CH_2)_4CH_3$, and $R_4$ is $—CH(OH)CH_3$;

$R_1$ is $—NHCO(2-thienyl)$, $R_2$ is $—OH$, $R_3$ is $CO(p-C_6H_4)_3O(CH_2)_4CH_3$, and $R_4$ is $—CH(OH)CH_3$;

$R_1$ is $—NHCO(4-pyridinyl)$, $R_2$ is $—OH$, $R_3$ is $CO(p-C_6H_4)_3O(CH_2)_4CH_3$, and $R_4$ is $—CH(OH)CH_3$;

$R_1$ is $—NHCO(4-piperidinyl)$, $R_2$ is $—OH$, $R_3$ is $CO(p-C_6H_4)_3O(CH_2)_4CH_3$, and $R_4$ is $—CH(OH)CH_3$;

$R_1$ is $—NHCO(2-tetrahydrofuroyl)$, $R_2$ is $—OH$, $R_3$ is $CO(p-C_6H_4)_3O(CH_2)_4CH_3$, and $R_4$ is $—CH(OH)CH_3$;

$R_1$ is $—NHCOOCH_3$, $R_2$ is $—OH$, $R_3$ is $CO(p-C_6H_4)_3O(CH_2)_4CH_3$, and $R_4$ is $—CH(OH)CH_3$;

$R_1$ is $—NHCOCH_2CH=CH_2$, $R_2$ is $—OH$, $R_3$ is $CO(p-C_6H_4)_3O(CH_2)_4CH_3$, and $R_4$ is $—CH(OH)CH_3$;

$R_1$ is $—NHCOCH_3$, $R_2$ is $—OH$, $R_3$ is $CO(p-C_6H_4)_3O(CH_2)_4CH_3$, and $R_4$ is $—CH(OH)CH_3$;

$R_1$ is $—NHCONHN(CH_3)_2$, $R_2$ is $—OH$, $R_3$ is $CO(p-C_6H_4)_3O(CH_2)_4CH_3$, and $R_4$ is $—CH(OH)CH_3$;

$R_1$ is $—NHCONHCH_2CH_2N(CH_3)_2$, $R_2$ is $—OH$, $R_3$ is $CO(p-C_6H_4)_3O(CH_2)_4CH_3$, and $R_4$ is $—CH(OH)CH_3$;

$R_1$ is $—NHCH_2CH(NH_2)CH_2OH$, $R_2$ is $—OH$, $R_3$ is $CO(p-C_6H_4)_3O(CH_2)_4CH_3$, and $R_4$ is $—CH(OH)CH_3$;

$R_1$ is $—NHCO(CH_2)_2COOH$, $R_2$ is $—OH$, $R_3$ is $CO(p-C_6H_4)_3O(CH_2)_4CH_3$, and $R_4$ is $—CH(OH)CH_3$;

$R_1$ is $—NHCOCH(NH_2)CH_2OH$, $R_2$ is $—OH$, $R_3$ is $CO(p-C_6H_4)_3O(CH_2)_4CH_3$, and $R_4$ is $—CH(OH)CH_3$;

$R_1$ is $—NHC=(NH)NH_2$, $R_2$ is $—OH$, $R_3$ is $CO(p-C_6H_4)_3O(CH_2)_4CH_3$, and $R_4$ is $—CH(OH)CH_3$;

$R_1$ is $—NHCOCH_2NH_2$, $R_2$ is $—OH$, $R_3$ is $CO(p-C_6H_4)_3O(CH_2)_4CH_3$, and $R_4$ is $—CH(OH)CH_3$;

$R_1$ is $—NHCOCH_2N(CH_3)_2$, $R_2$ is $—OH$, $R_3$ is $CO(p-C_6H_4)_3O(CH_2)_4CH_3$, and $R_4$ is $—CH(OH)CH_3$; and $R_1$ is $—NHCOCH_2N^+(CH_3)_3$, $R_2$ is $—OH$, $R_3$ is $CO(p-C_6H_4)_3O(CH_2)_4CH_3$, and $R_4$ is $—CH(OH)CH_3$.

The present invention discloses compositions comprising a therapeutically effective amount of a compound of the invention and a pharmaceutically acceptable carrier or diluent.

The compounds of the invention exhibit in vitro activity as antifungal agents against a variety of fungal organisms and inhibit (1,3)-β-glucan synthase. They are therefore expected to be useful in the treatment of fungal infections in mammals. When used in such treatment, a therapeutically effective amount of the compound of the present invention may be employed in pure form or, where such forms exist, in pharmaceutically acceptable salt, ester or prodrug form.

Alternatively, the compound may be administered as pharmaceutical compositions containing the compound of interest in combination with one or more pharmaceutically acceptable excipients. By a "therapeutically effective amount" of the compound of the invention is meant a sufficient amount of the compound to treat the targeted disorder, at a reasonable benefit/risk ratio applicable to any medical treatment, which is administered in such quantities and over such a period of time as is necessary to obtain the desired therapeutic effect. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compound of this invention administered to a human or lower animal may range from about 0.1 to about 100 mg/kg/day or for topical administration from about 0.1 to about 10% in cream, ointment or other topical formulation or for rectal or vaginal administration from about 10 to about 500 mg per dose in a suitable vehicle. For purposes of oral administration, doses may be in the range of from about 1 to about 100 mg/kg/day or, more preferably, of from about 10 to about 20 mg/kg/day. If desired, the effective daily dose may be divided into multiple doses for purposes of administration; consequently, single dose compositions may contain such amounts or submultiples thereof as make up the daily dose.

The pharmaceutical compositions of the present invention comprise a compound of the invention and a pharmaceutically acceptable carrier or excipient, which may be administered orally, rectally, parenterally, intracisternally, intravaginally, intraperitoneally, topically (as by powders, ointments, or drops), bucally, or as an oral or nasal spray. By "pharmaceutically acceptable carrier" is meant a non-toxic solid, semi-solid or liquid filler, diluent, encapsulating material or formulation auxiliary of any type. The term "parenteral" as used herein refers to modes of administration which include intravenous, intramuscular, intraperitoneal, intracisternal, subcutaneous and intraarticular injection and infusion.

Pharmaceutical compositions of this invention for parenteral injection include pharmaceutically acceptable sterile nonaqueous solutions or aqueous dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose and acacia, c) humectants such as glycerol, d) disintegrating agents such as agar-agar, calcium carbonate, potato or tapioca starch, alginic acid, certain silicates and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols and sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, olive, castor and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, and sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Topical administration includes administration to the skin or mucosa, including surfaces of the lung and eye. Compositions for topical administration, including those for inhalation, may be prepared as a dry powder which may be pressurized or non-pressurized. In non-pressurized powder compositions, the active ingredient in finely divided form may be used in admixture with a larger-sized pharmaceutically acceptable inert carrier comprising particles having a size, for example, of up to 100 micrometers in diameter. Suitable inert carriers include sugars such as lactose. Desirably, at least 95% by weight of the particles of the active ingredient have an effective particle size in the range of 0.01 to 10 micrometers.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

Alternatively, the composition may be pressurized and contain a compressed gas, such as nitrogen or a liquified gas propellant. The liquified propellant medium and indeed the total composition is preferably such that the active ingredient does not dissolve therein to any substantial extent. The pressurized composition may also contain a surface active agent. The surface active agent may be a liquid or solid non-ionic surface active agent or may be a solid anionic surface active agent. It is preferred to use the solid anionic surface active agent in the form of a sodium salt.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

The compound of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., *Methods in Cell Biology*, Volume XIV, Academic Press, New York, N.Y., 1976, p. 33 et seq.

In yet another aspect of the present invention are disclosed processes useful in the preparation of the above compounds represented in Scheme 1 below.

The cyclic hexapeptides have been synthesized either via solid phase peptide synthesis or solution phase peptide synthesis. In Scheme 1, BHA Resin and linker molecule bearing the homotyrosine (Hty) residue, protected with fluorenylmethyloxycarbonyl (Fmoc) and trimethylsilylethyl (Tse), are combined and coupled to load the protected Hty residue giving new resin 1. Each subsequent residue is deprotected (removal of Fmoc group occurs with 20% piperidine) to afford a free amine terminus, followed by coupling to the next aminoacid. Once tetrapeptide 8 is obtained, the α-amine is again deprotected and coupled, in this case, with the acid sidechain 9 activated as its trichlorophenyl ester or with an aldehyde via reductive alkylation using sodium cyanoborohydride. Deprotection of the N-terminal allyloxycarbonyl (Aloe) group allows for addition of the next two amino acid residues, e.g. azidoproline and threonine, with the latter being added as its N-t-butoxycarbonyl (Boc) analog. Deprotection of the linear hexapeptide with trifluoroacetic acid then produces aminoacid 16. Cyclization followed by deprotection of any extraneous sidechain protecting groups then leads to final products 18.

The aminoacid residues are either commercially available or readily prepared in protected form using organic synthetic methods known in the art.

Scheme 1
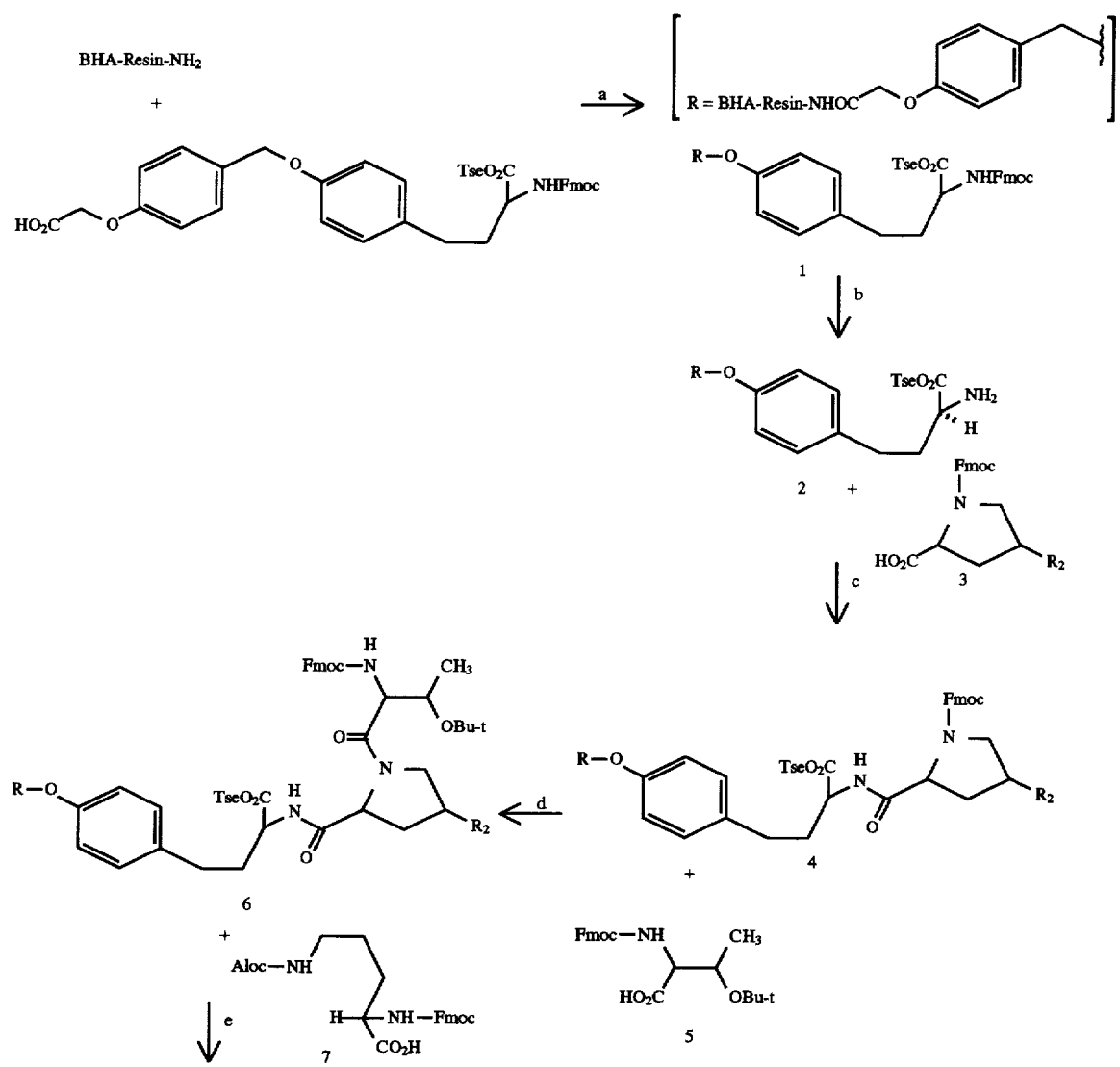

5,696,084
15 16
-continued
Scheme 1
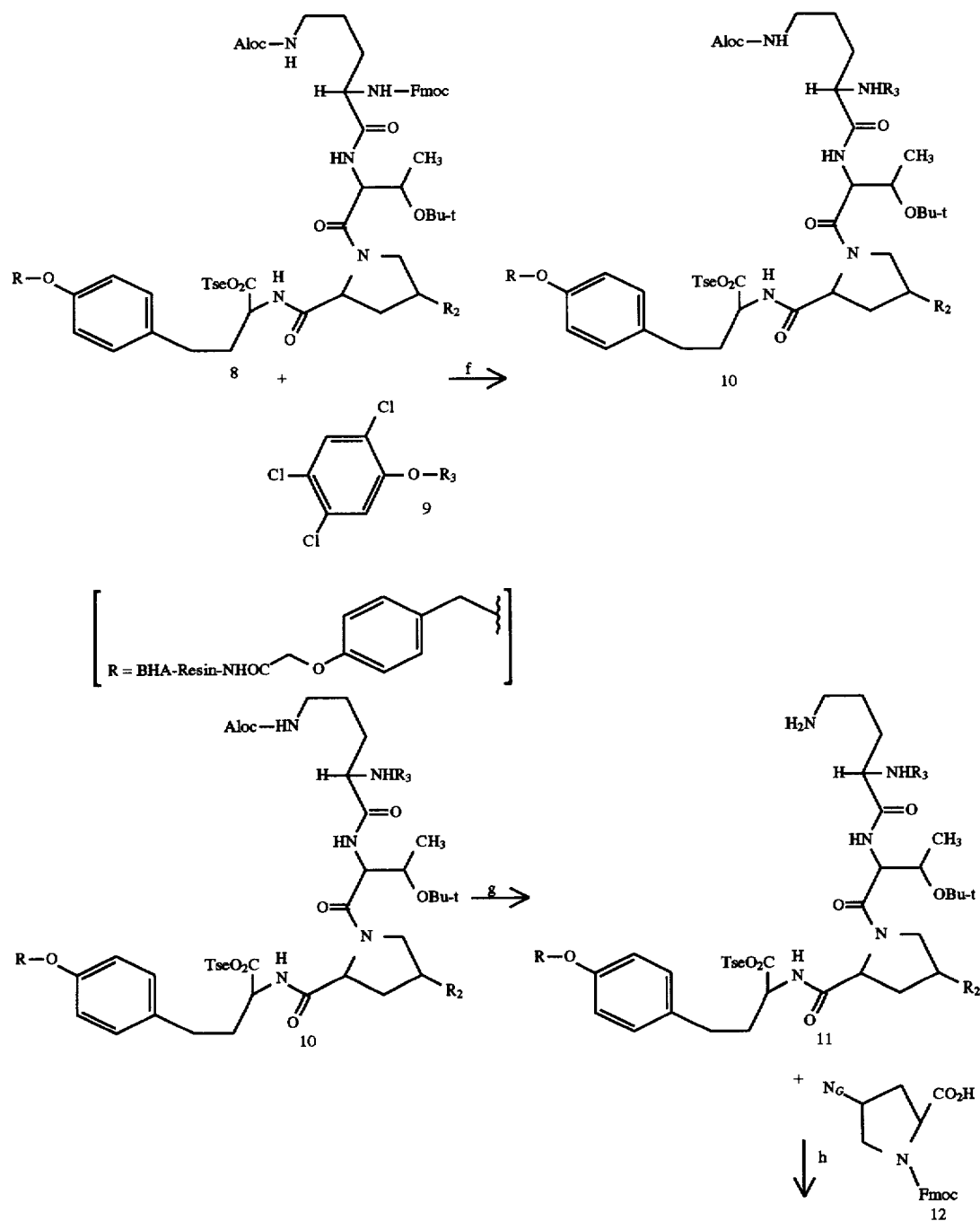

-continued
Scheme 1

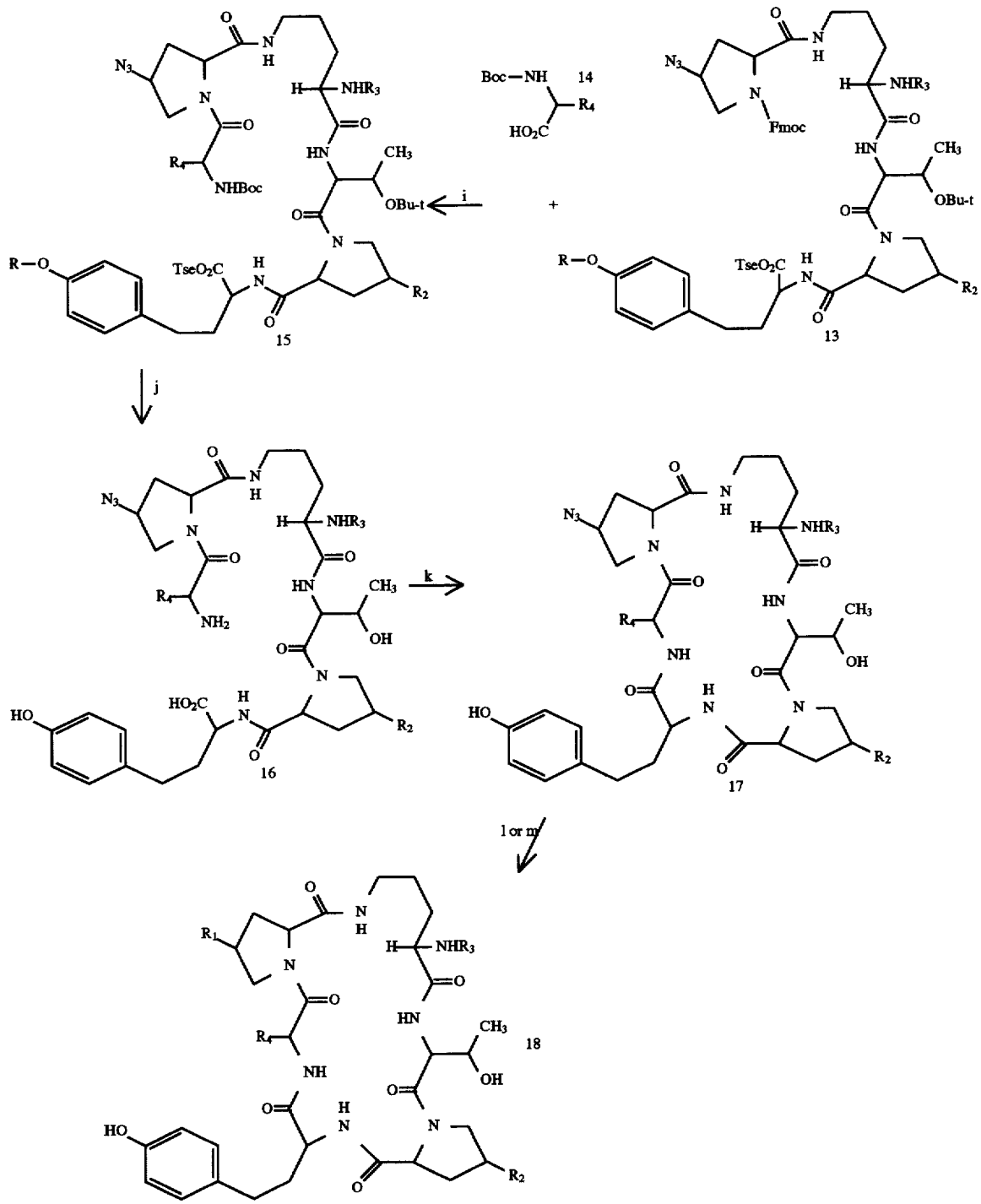

The compounds, processes and uses of the present invention will be better understood in connection with the following examples, which are intended as an illustration of and not a limitation upon the scope of the invention. The following abbreviations were used: Hty for homotyrosine; EtOAc for ethyl acetate; EtOH for ethanol; MeOH for methanol; THF for tetrahydrofuran; TLC for thin layer chromatography; DCM=dichloromethane; DMF=dimethylformamide; DIPEA=diisopropylethylamine; HOBT=N-hydroxybenzo- triazole; DIPC=diisopropylcarbodiimide; NMP=N-methyl pyrrolidone; PyBOP=Benzotriazole-1-yl-oxy-tris- pyrrolidino-phosphoniumhexa-fluorophosphate.

GENERAL PROCEDURES FOR SOLID PHASE PEPTIDE SYNTHESIS

Step 1(a)

The Hty-linker portion is loaded onto the resin in the following manner:

To the Hty-linker in DCM:NMP (40 mL; 3:1) is added 1.2 eq. HOBT at 0° C. in a separatory funnel followed by 1.2 eq. of DIPC. After 30 minutes this mixture is added to base-washed BHA resin (Novabiochem; 0.6–0.9 mmol/g) and rinsed with more DCM (10 mL). This mixture is shaken overnight and washed the following day three times with 50 mL DCM (for 5 minutes) followed by 50 mL MeOH (for 5 minutes). Endcapping was carried out by shaking the resin with acetic anhydride (4 eq./mole of resin) overnight followed by washing three times consecutively with 50 mL DCM (for 5 minutes), 50 mL DMF (for 5 minutes), and 50 mL MeOH (for 5 minutes) to give resin 1 after drying by vacuum evaporation. The loading number was calculated to be 0.46 mmol/gram of resin.

Step 1(b)

The resin 1 from above is washed twice with 75 mL DMF (for 5 minutes), treated with 75 mL 20% piperidine in DMF twice (@15 minutes) and washed with 50 mL DMF six times (for 5 minutes) to give resin 2.

Step 1(c)

To the resin 2 is added 3 eq. of FmoctHyp(t-Bu)OH 3, 3.3 eq. of HOBT, and 3.3 eq. of DIPC along with NMP (40 mL). This mixture is shaken overnight. The next day the resulting resin 4 is washed consecutively three times with 50 mL DMF (for 5 minutes), 50 mL DCM (for 5 minutes), and 50 mL DMF:DCM (1:1) (for 5 minutes).

Step 1(d)

Resin 4 is treated as in Step 1(b) above followed by combining with 3 eq. Fmoc-threonine 5, 3.3 eq. HOBT, 3.3 eq. DIPC along with 50 mL NMP. After shaking overnight the resin 6 so obtained is washed consecutively three times with 50 mL DMF (for 5 minutes), 50 mL DCM (for 5 minutes), and 50 mL DMF:DCM (1:1) (for 5 minutes).

Step 1(e)

Resin 6 is treated as in Step 1(b) above followed by combining with 2 eq. Fmoc-Ornithine(Aloc)OH 7, 2.2 eq. HOBT, 2.2 eq. DIPC along with 50 mL NMP. After shaking overnight this resin is washed consecutively three times with 50 mL DMF (for 5 minutes), 50 mL DCM (for 5 minutes), and 50 mL DMF:DCM (1:1) (for 5 minutes) and dried to give the peptide resin 8.

Step 1(f)

Resin 8 from Step 1(e) above is treated as in Step 1(b) above followed by combining with 2 eq. of trichlorophenylester 9, 1.2 eq. DIPEA along with 50 mL NMP. This mixture is shaken on a rotovap in a water bath heated to 60° C. overnight. The next day it is washed consecutively three times with 50 mL DMF (for 5 minutes), 50 mL DCM (for 5 minutes), and 50 mL DMF:DCM (1:1) (for 5 minutes) to give resin 10.

Step 1(g)

Resin 10 is treated with 3 eq. tri-n-butyltin hydride, 1.5 mL HOAc, 40 mL DCM and 0.04 eq. Pd(Ph$_3$P)$_4$. After shaking over night this resin is washed consecutively twice with 50 mL DCM (for 5 minutes), 50 mL 10% TEA in DCM (for 5 minutes), 50 mL DCM (for 5 minutes), 50 mL MeOH (for 5 minutes), and 50 mL DCM (for 5 minutes) to give dried resin 11.

Step 1(h)

Resin 11 is treated with 4.4 eq. of the azido-Hyp replacement 12, 4 eq. HOBT, 4 eq. DIPC in NMP. After shaking overnight resin 13 is washed consecutively three times with 50 mL DMF (for 5 minutes), 50 mL DCM (for 5 minutes), and 50 mL DMF:DCM (1:1) (for 5 minutes).

Step 1(i)

Resin 13 is treated as in Step 1(b) above followed by combining with a Boc-protected threonine (Thr) replacement 14, 4 eq. HOBT, 4 eq. DIPC in NMP. After shaking overnight the resin 15 so obtained is washed consecutively three times with 50 mL DMF (for 5 minutes), 50 mL DCM (for 5 minutes), and 50 mL DMF:DCM (1:1) (for 5 minutes) to give 15.

Step 1(j).

Resin 15 is shaken with 90% TFA for 2–3 h, the resin is filtered and rinsed with more 90% TFA, and the TFA washings are collected and evaporated. The residue is triturated with ether, and the solids are filtered and dried to give 16.

Step 1(k)

To a solution of 16 from Step 1(j) above in 10 mL of DMF is added 2.5 eq. HOBT, 5 eq. DIPEA, and 2.5 eq. of PyBOP and stirred overnight at 25° C. The next day the DMF is evaporated, the residue is dissolved in MeOH and precipitated by adding water or ether. The crude solids are filtered and dried before purification by HPLC or flash chromatography on silica gel to give the cyclic hexapeptide 17.

Step 1(l)

Resin 17 is shaken with 10% Pd/C for 2–3 h in THF with a hydrogen balloon, and the mixture is filtered, rinsed with more MeOH, and the washings are collected and evaporated. The residue is triturated with ether, the crude solids are filtered and dried before purification by HPLC or flash chromatography on silica gel to give the final cyclic hexapeptide 18.

Step 1(m)

Alternatively, resin 17 is refluxed in 20% aqueous THF with 4 eq. of triphenylphosphine and evaporated. The crude solids are purified by HPLC or flash chromatography on silica gel to give the final cyclic hexapeptide 18.

EXAMPLES 1–12

Compounds 1–12 represented by formula II, wherein R$_1$ is —NH$_2$, R$_2$ is —OH, R$_3$ is —CO(p-C$_6$H$_4$)$_3$O(CH$_2$)$_4$CH$_3$ and R$_4$ is as defined in Table 1 below, were prepared in accordance with the steps 1(a) through 1(l) described above.

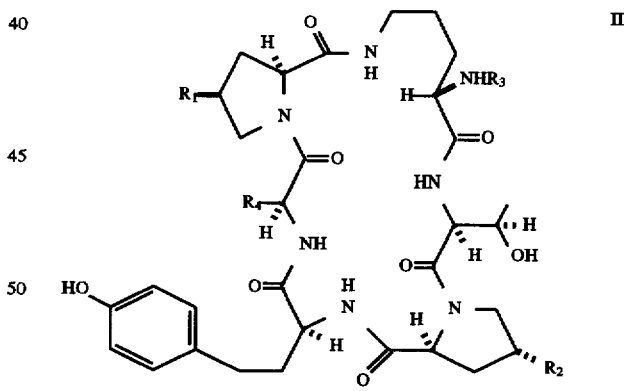

The Hty linker portion was loaded on to the BHA-resin-NH$_2$ residue and treated as described in steps 1(a) and 1(b) above, in the general procedure for solid phase peptide synthesis to obtain resin 2. Resin 2 was then reacted with Fmoc-(L)-trans-hydroxyproline t-butyl ether (3) in step 1(c) to obtain resin 4. Resin 4 was coupled with Fmoc-(L)-threonine t-butyl ether (5) and Fmoc-(L)-ornithine(Aloc) (7) as set forth in steps 1(d) through 1(e) to obtain resin 8. Resin 8 was reacted with the trichlorophenylester of (4"-pentyloxy)terphenyl-carboxylic acid 9 as described in step 1(f) to afford resin 10. Resin 10 was treated as described in step 1(g) to yield resin 11, which was, in turn, reacted with Fmoc-(L)-cis-4-azidoproline 12 as described in step (h) to obtain resin 13. Resin 13 was condensed with Boc-(L)-threonine 14 or other amino acids with sidechains shown in Table 1 as described in step (i) to obtain resin 15. Where a sidechain amine was protected by a carbobenzyloxy group or an acid protected by benzyl ester, either was deprotected via standard hydrogenolysis chemistry using hydrogen and palladium on charcoal. Resin 15 was then treated as described in steps 1(j) through 1(l) to obtain the final compounds 18 listed in Table 1. The analytical data confirming the structures of compounds 1–18 are also provided in Table 1 below.

TABLE 1

| Example No. | $R_4$ | Mass Spectra (FAB) m/z | HRMS Calculated For | HRMS Measured | HPLC %/RT |
|---|---|---|---|---|---|
| 1 | HO—CH(H···)(H₃C)— | [M+H⁺] 1061 | — | — | 100/13.5 |
| 2 | HO— (ethyl) | 1085 [M+K⁺] | $C_{56}H_{70}N_8O_{12}K$ 1085.4750 | 1085.4745 | 98/13.2 |
| 3 | H₃C— (isopropyl) | 1083 [M+K⁺] | $C_{57}H_{72}N_8O_{11}K$ 1083.4958 | 1083.4937 | 99/13.8 |
| 4 | $NH_2$—(CH₂)₃— | 1112 [M+K⁺] | $C_{58}H_{75}N_9O_{11}K$ 1112.5223 | 1112.5223 | 100/11.4 |
| 5 | $NH_2$—(CH₂)₄— | 1126 [M+K⁺] | $C_{59}H_{77}N_9O_{11}K$ 1126.5380 | 1126.5363 | 100/11.5 |
| 6 | $NH_2$—CH₂— | 1084 [M+K⁺] | $C_{56}H_{72}N_9O_{11}$ 1046.5351 | 1046.5347 | 96/12.5 |
| 7 | $H_2N$-C(NH)-NH-(CH₂)₃— | 1116 [M+K⁺] | $C_{59}H_{78}N_{11}O_{11}$ 1116.5882 | 1116.5880 | 95/12.1 |
| 8 | $H_3C$— | 1031 [M+H⁺] | $C_{56}H_{71}N_8O_{11}$ 1031.5242 | 1031.5227 | 100/13.6 |
| 9 | HO—C₆H₄—CH₂— | 1055 [M+K⁺] | $C_{55}H_{68}N_8O_{11}K$ 1055.4645 | 1055.4653 | 97/13.2 |
| 10 | H— | 1089 [M+H⁺] | $C_{58}H_{73}N_8O_{13}$ 1089.5297 | 1089.5293 | 100/13.2 |
| 11 | $HO_2C$—(CH₂)₂— | 1075 [M+H⁺] | $C_{57}H_{71}N_8O_{13}$ 1075.5141 | 1075.5162 | 98/13.5 |
| 12 | $HO_2C$—CH₂— | 1123 [M+H⁺] | $C_{62}H_{75}N_8O_{12}$ 1123.5504 | 1123.5470 | 99/14.1 |

EXAMPLES 13–14

Compounds 13 and 14 represented by formula II, wherein $R_1$ is —$NH_2$, $R_2$ is as defined in Table 2 below, $R_3$ is —$CO(p-C_6H_4)_3O(CH_2)_4CH_3$ and $R_4$ is as defined in Example 1 above, were prepared as described above in steps 1(a) through 1(l) using an appropriate amino acid residue 3 in step 1(c). The amino acid residue 3 is defined by substituent $R_2$ listed in Table 2.

TABLE 2

| Example No. | $R_2$ | Mass Spectra (FAB) m/z | HRMS Calculated For | HRMS Measured | HPLC %/RT |
|---|---|---|---|---|---|
| 13 | H | 1045 [M + H]⁺ | $C_{57}H_{73}N_8O_{11}$ 1045.5399 | 1045.5406 | 80/16.9 |
| 14 | F | 1063 [M + H]⁺ | $C_{57}H_{72}FN_8O_{11}$ 1063.5304 | 1063.5304 | 99/16.7 |

TABLE 2-continued

| Example No. | $R_2$ | Mass Spectra (FAB) m/z | HRMS Calculated For | HRMS Measured | HPLC %/RT |
|---|---|---|---|---|---|
| | | | 1063.5305 | | |

EXAMPLES 15–23

Compounds 15–23 represented by formula II wherein $R_1$ is —$NH_2$, $R_2$ is —OH, $R_3$ is as defined in Table 3 below and $R_4$ is as defined in Example 1 above, were prepared as described above in steps 1(a) through 1(l) using an appropriate trichlorophenyl ester 9 in step 1(f). The ester 9 is defined by the substituent $R_3$ listed in Table 3 below. Theses esters were prepared via standard methods described in WO 96/11210 published Apr. 18, 1996.

TABLE 3

| Example No. | R₃ | Mass Spectra (FAB) m/z | HRMS Calculated For | Measured | HPLC %/RT |
|---|---|---|---|---|---|
| 15 | (4-acetylphenyl)-piperazine-N-octyl | [M+H+] 1019 | — | — | 91.7/4.94 |
| 16 | (4-acetylphenyl)-piperazine-N-(4-octyloxyphenyl) | [M+H+] 1111 | $C_{58}H_{83}N_{10}O_{12}$ 1111.6192 | 1111.6188 | 92.8/10.0 |
| 17 | (4-acetylphenyl)-piperazine-N-(4-methoxyphenyl) | [M+H+] 1013 | — | — | — |
| 18 | (4-acetylphenyl)-piperazine-N-(4-heptyloxyphenyl) | [M+H+] 1069 | $C_{55}H_{77}N_{10}O_{12}$ 1069.5722 | 1069.5726 | 93.2/5.60 |
| 19 | 4-(octyloxy)phenyl acetate | [M+H+] 967 | $C_{48}H_{70}N_{8}O_{13}$ 967.5141 | 967.5148 | 90.6/9.90 |

TABLE 3-continued

| Example No. | R₃ | Mass Spectra (FAB) m/z | HRMS Calculated For | Measured | HPLC %/RT |
|---|---|---|---|---|---|
| 20 | [4-acetylphenoxy-heptyl group] | [M+H+] 951 | $C_{48}H_{71}N_8O_{12}$ 951.5191 | 951.5190 | 93.6/9.02 |
| 21 | [4-ethoxyphenoxy-heptyl group] | [M+H+] 937 | $C_{48}H_{72}N_8O_{11}$ 937.5399 | 937.5422 | 64.7/5.91 |
| 22 | [4-acetylpiperazinyl-biphenyl-methoxy group] | [M+H+] 1013 | $C_{51}H_{69}N_{10}O_{12}$ 1013.5096 | 1013.5096 | 90.9/8.36 |
| 23 | [4-ethyl-terphenyl-oxy-pentyl group] | 1047 [M+H⁺] | $C_{57}H_{75}N_8O_{11}$ 1047.5555 | 1047.5554 | 90/11.5 |

EXAMPLES 24–52

Compounds 24–52 represented by formula II, wherein $R_1$ is $-NR_5R_6$, $R_2$ $-OH$, $R_3$ is $-CO(p-C_6H_4)_3O(CH_2)_4CH_3$ and $R_4$ is as defined in Example 1 above, were prepared in the manner described in steps 1(a) through 1(m) above by reducing the azido group in 17 in step (m). The resulting primary amino group was subsequently acylated with commercially available active esters or reductively alkylated with commercially available aldehydes and sodium cyanoborohydride under standard conditions by methods known in the art to produce the correspondingly substituted compounds listed below in Table 4.

TABLE 4

| Example No. | R₅ | R₆ | Mass Spectra (FAB) m/z | HRMS Calculated For | Measured | HPLC %/RT |
|---|---|---|---|---|---|---|
| 24 | CH₃ | H | 1075 [M+H⁺] | — | — | 100/14.4 |
| 25 | CH₃ | CH₃ | 1089 [M+H⁺] | — | — | 74/16.3 |
| 26 | CH₃ | Ac | 1117 [M+H⁺] | $C_{60}H_{77}N_8O_{13}$ 1117.561 | 1117.5605 | 96/15.156 |
| 27 | PHCH₂ | H | 1151 [M+H⁺] | — | — | 83/17.656 |

TABLE 4-continued
| Example No. | $R_5$ | $R_6$ | Mass Spectra (FAB) m/z | HRMS Calculated For | HRMS Measured | HPLC %/RT |
|---|---|---|---|---|---|---|
| 28 | 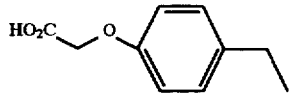 | H | 1225 [M+H⁺] | — | — | 14.918 |
| 29 | 4—Py—CH₂ | H | 1152 [M+H⁺] | $C_{63}H_{78}N_9O_{12}$ 1152.5403 | 1152.5795 | 95/15.936 |
| 30 | HO₂CCH₂ | H | 1119 [M+H⁺] | $C_{59}H_{75}N_8O_{14}$ 1119.5403 | 1119.5410 | 86/13.808 |
| 31 | Acyl | H | 1103 [M+H⁺] | — | — | 100/14.731 |
| 32 | 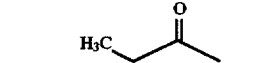 | H | 1117 [M+H⁺] | $C_{60}H_{74}N_8O_{13}$ 1117.5610 | 1117.5610 | 89/15.678 |
| 33 | 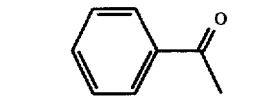 | H | 1203 [M+K⁺] | $C_{64}H_{77}N_8O_{13}$ 1165.5610 | 1165.5626 | 76/18.571 |
| 34 | 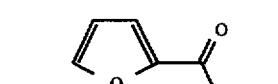 | H | 1155 [M+H⁺] | $C_{62}H_{75}N_8O_{14}$ 1155.5403 | 1155.5426 | 80/16.806 |
| 35 | 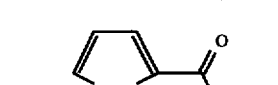 | H | 1171 [M+H⁺] | $C_{62}H_{75}N_8O_{13}S$ 1171.5174 | 1171.5194 | 94/18.058 |
| 36 |  | H | 1166 [M+H⁺] | $C_{63}H_{76}N_9O_{13}$ 1166.5593 | 1166.5569 | 98/13.2 |
| 37 | 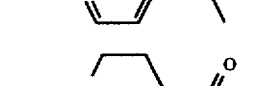 | H | 1172 [M+H+] | — | — | 80/13.0 |
| 38 |  | H | 1159 [M+H⁺] | — | — | 87/16.243 |
| 39 | 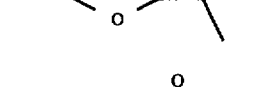 | H | 1119 [M+H⁺] | $C_{59}H_{75}N_8O_{14}$ 1119.5403 | 1119.5410 | 90/15.9 |
| 40 | 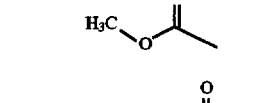 | H | 1145 [M+H⁺] | — | — | 100/17.615 |
| 41 | 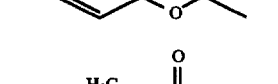 | H | 1156 [M+K⁺] | $C_{59}H_{76}N_9O_{13}$ 1118.5563 | 1118.5575 | 97/14.6 |
| 42 | 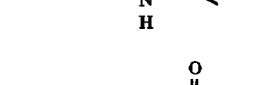 | H | 1147 [M+H⁺] | $C_{60}H_{79}N_{10}O_{13}$ 1147.5828 | 1147.5812 | 72/14.6 |
| 43 | 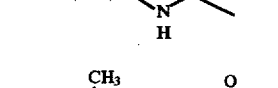 | H | 1175 [M+H⁺] | — | — | 88/13.7 |

TABLE 4-continued

| Example No. | R₅ | R₆ | Mass Spectra (FAB) m/z | HRMS Calculated For | Measured | HPLC %/RT |
|---|---|---|---|---|---|---|
| 44 | CH₂=N-NH-C(NH₂)-CH₂-C(=O)-CH₃ structure | H | 1198 [M+H⁺] | $C_{63}H_{80}N_{11}O_{13}$ 1198.5937 | 1198.5953 | 81/12.38 |
| 45 | $H_2N$-CH₂-CH₂-CH₂-CH(NH₂)-C(=O)-CH₃ | H | 1175 [M+H⁺] | $C_{62}H_{83}N_{10}O_{13}$ 1175.6128 | 1175.6141 | 72/13.581 |
| 46 | $HO_2C$-CH₂-CH₂-C(=O)-CH₃ | H | 1161 [M+H⁺] | $C_{61}H_{77}N_8O_{15}$ 1161.5508 | 1161.5491 | 95/13.7 |
| 47 | HO-CH₂-CH(NH₂)-CH₂-CH₃ | H | 1134 [M+H⁺] | — | — | 98/12.128 |
| 48 | HO-CH₂-CH(NH₂)-C(=O)-CH₃ | H | 1148 [M+H⁺] | $C_{60}H_{78}N_9O_{14}$ 1148.5668 | 1148.5698 | 82/12.5 |
| 49 | $H_2N$-C(=NH)-CH₃ | H | 1103 [M+H⁺] | $C_{58}H_{75}N_{10}O_{12}$ 1103.5566 | 1103.5544 | 88/14.2 |
| 50 | $H_2N$-CH₂-C(=O)-CH₃ | H | 1118 [M+H⁺] | — | — | 100/13.0 |
| 51 | $(CH_3)_2N$-CH₂-C(=O)-CH₃ | H | 1146 [M+H⁺] | $C_{61}H_{80}N_9O_{13}$ 1146.5876 | 1146.5887 | 79/13.701 |
| 52 | I⁻ $(CH_3)_3N^+$-CH₂-C(=O)-CH₃ | H | 1160 [M⁺] | $C_{62}H_{82}N_9O_{13}$ 1160.6032 | 1160.6022 | 63/13.701 |

IN VITRO ASSAY OF ANTIFUNGAL ACTIVITY

Minimal inhibitory concentrations (MICs) were determined by the broth microdilution method. The test compounds and the control amphotericin B were dissolved in appropriate solvents and then serially diluted in Yeast Nitrogen Broth medium supplemented with glucose in 50 µl volumes in microtiter plates. Yeast cultures were grown on Sabouraud dextrose agar for 18 hours at 35° C. Colonies were suspended in saline to the turbidity equivalent to a McFarland 0.5 standard and then further diluted 1:50 in Yeast Nitrogen Broth. Filamentous fungi were grown under the same conditions. Spores were harvested, resuspended in saline at approximately 106 CFU/ml, and then diluted 1:50 in Yeast Nitrogen broth. The microtiter trays were inoculated with 50 µl of the fungal suspensions and incubated for 24 to 48 hr. Inhibition of growth was determined visually. The results demonstrate that the compounds of the present invention possess significant antifungal activity.

| Example No. | MIC (mcg/mL) Candida albicans ATCC 10231 | ATCC 38247 | Example No. | MIC (mcg/mL) Candida albicans ATCC 10231 | ATCC 38247 |
|---|---|---|---|---|---|
| 1 | 0.2 | 0.1 | 27 | 0.78 | 6.25 |
| 2 | 0.1 | 0.2 | 28 | 0.78 | 3.12 |
| 3 | 0.1 | 0.39 | 29 | 0.39 | 6.25 |
| 4 | 0.39 | 0.39 | 30 | 0.39 | 6.25 |
| 5 | 0.2 | 0.39 | 31 | 0.2 | 0.39 |
| 6 | 0.78 | 0.78 | 32 | 0.39 | 3.12 |
| 7 | 0.39 | 0.78 | 33 | 6.25 | 25.00 |
| 8 | 0.2 | 0.39 | 34 | 0.39 | 12.5 |
| 9 | 0.78 | 1.56 | 35 | 3.12 | 50.00 |
| 10 | 0.39 | 1.56 | 36 | 0.39 | 6.25 |
| 11 | 0.39 | 1.56 | 37 | 0.39 | 1.56 |
| 12 | 0.39 | 1.56 | 38 | 0.78 | 6.25 |
| 13 | 0.39 | 0.39 | 39 | 0.78 | 1.56 |
| 14 | 0.39 | 3.12 | 40 | 3.12 | >100 |
| 15 | 1.56 | 3.12 | 41 | 0.39 | 0.78 |
| 16 | 0.2 | 0.2 | 42 | 1.56 | 6.25 |
| 17 | 3.12 | 12.5 | 43 | 0.78 | 1.56 |
| 18 | 0.2 | 0.2 | 44 | 0.39 | 0.78 |
| 19 | 3.12 | 1.56 | 45 | 0.78 | 1.56 |
| 20 | 0.39 | 0.39 | 46 | 0.78 | 3.12 |
| 21 | 0.78 | 0.2 | 47 | 0.39 | 0.78 |
| 22 | 6.25 | 6.25 | 48 | 0.78 | 1.56 |

-continued

| Example No. | MIC (mcg/mL) Candida albicans ATCC 10231 | MIC (mcg/mL) Candida albicans ATCC 38247 | Example No. | MIC (mcg/mL) Candida albicans ATCC 10231 | MIC (mcg/mL) Candida albicans ATCC 38247 |
|---|---|---|---|---|---|
| 23 | 0.39 | 0.2 | 49 | 0.2 | 0.39 |
| 24 | 0.2 | 0.39 | 50 | 0.39 | 0.78 |
| 25 | 12.5 | 25.00 | 51 | 0.39 | 0.78 |
| 26 | 0.78 | 6.25 | 52 | 1.56 | 6.25 |

IN VIVO ASSAY OF ANTIFUNGAL ACTIVITY

The cyclic peptides were evaluated in an acute systemic model of C. albicans infection. Mice were inoculated intravenously with a $10^0$ dilution ($1-5 \times 10^6$ cfu/mouse) of a 24 hour culture of C. albicans CAF2 grown in Sabauroud broth. Medications were initiated at 1 hour post inoculation by intraperitoneal injection. Mice were monitored daily for survival for 10 days. Curative therapy was determined by plating kidney homogenates of surviving mice on Sabouraud agar. Mortality was recorded for 10 days, and the mean effective dose sufficient to protect 50% of the mice ($ED_{50}$) was calculated from the cumulative mortality by trimmed-logit analysis.

| Example No. | $ED_{50}$ (mg/kg) Candida albicans CAF2 |
|---|---|
| 1 | 22.9 |
| 2 | 12.5 |
| 3 | 18.4 |
| 4 | <5.0 |
| 6 | 21.79 |
| 7 | 7.74 |
| 16 | 4.81 |
| 18 | 20.6 |
| 23 | 10.0 |
| 27 | 6.05 |
| 52 | 7.98 |

From the above data, it is evident that the compounds of the invention will be effective for treatment of fungal infections in human or veterinary patients.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art, and may be made without departing from the spirit and scope thereof.

What is claimed is:
1. A compound having the formula:

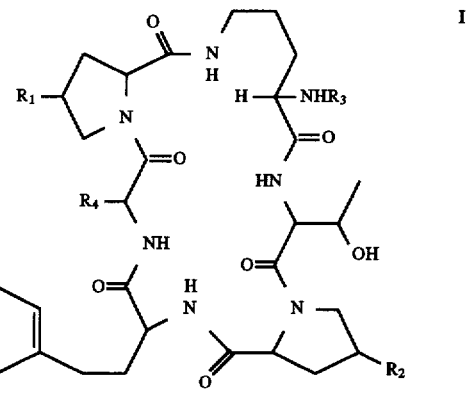

or a pharmaceutically acceptable acid, ester or prodrug thereof, wherein $R_1$ is $NR_5R_6$ or $-CH_2NH_2$;

$R_2$ is selected from the group consisting of hydrogen, hydroxyl, halo, and amino;

$R_3$ is selected from the group consisting of $-COR_7$, $-COOR_7$, or $-CH_2R_7$;

$R_4$ is selected from the group consisting of hydrogen, alkyl, hydroxyalkyl, aminoalkyl, di- and trialkylaminoalkyl, p-hydroxyaryl(alkyl), guanidinoalkyl, carboxyalkyl, arylalkyl and heteroarylalkyl;

$R_5$ and $R_6$ are independently at each occurrence selected from the group consisting of hydrogen, lower alkyl, arylalkyl, aminoalkyl, hydroxy(aminoalkyl), carboxyalkyl, di- and trialkylaminoalkyl, guanidinyl, and $-COR_8$, or taken together with atoms to which each is attached, $R_5$ and $R_6$ form a 5- or 6-membered ring containing one nitrogen atom;

$R_7$ is selected from the group consisting of aryl, aryl-aryl, aryl-aryl-aryl, arylalkyl, alkylaryl, arylalkoxy, aryl-hetero-aryl, hetero-aryl-aryl, aryl-aryl-hetero, and aryl-hetero-alkyl, wherein hetero group is selected from the group consisting of furyl, homopiperidinyl, morpholinyl, piperazinyl, piperidinyl, pyrazinyl, pyridazinyl, pyridyl, pyrimidinyl, pyrrolidinyl, pyrrolyl, quinolinyl, and thienyl; and $R_8$ is selected from the group consisting of lower alkyl, mono-, di- and trialkylaminoalkyl, hydroxy(aminoalkyl), carboxyalkyl, hetero(alkylaminoalkyl), hydrazinyl, alkenyloxy, heterocyclic, heteroaromatic, alkoxy, aryl, and arylalkyl.

2. A compound according to claim 1 wherein $R_2$ is selected from the group consisting of hydrogen, fluoro, and hydroxyl.

3. A compound according to claim 1 wherein $R_4$ is selected from the group consisting of $-CH(OH)CH_3$, $-CH_2OH$, $-CH_2CH_3$, $-CH_2(CH_2)_nNH_2$, $-CH_2(CH_2)_n(NH)C=(NH)-NH_2$, $-CH_3$, $-CH_2(C_6H_5)OH$, hydrogen, $-CH_2CH_2COOH$, and $-CH_2COOH$, where n is from 0 to 5.

4. A compound according to claim 1, wherein $R_1$ is $-NH_2$.

5. A compound according to claim 4, wherein $R_4$ is selected from the group consisting of $-CH_2OH$, $-CH_2CH_2CH_2NH_2$, $-CH_2NH_2$ and $-CH(OH)CH_3$.

6. A compound according to claim 5, wherein $R_2$ is hydroxyl.

7. A compound according to claim 6, wherein $R_3$ is —(p-$C_6H_4$)$_3$O($CH_2$)$_4CH_3$, or —(p-$C_6H_4$)(Piperazinyl)(p-$C_6H_4$)O($CH_2$)$_7CH_3$.

8. A compound of formula II:

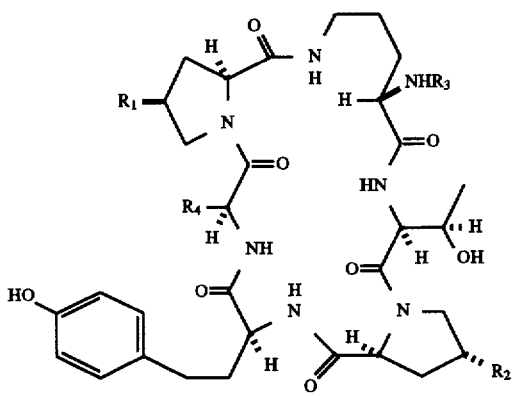

or a pharmaceutically acceptable acid, ester or prodrug thereof, wherein $R_1$ is —$NH_2$, $R_2$ is —OH, $R_3$ is —CO(p-$C_6H_4$)$_3$O($CH_2$)$_4CH_3$, and $R_4$ is —$CH_2OH$;

$R_1$ is —$NH_2$, $R_2$ is —OH, $R_3$ is —CO(p-$C_6H_4$)$_3$O($CH_2$)$_4CH_3$, and $R_4$ is —CH(OH)$CH_3$;

$R_1$ is —$NH_2$, $R_2$ is —OH, $R_3$ is —CO(p-$C_6H_4$)$_3$O($CH_2$)$_4CH_3$, and $R_4$ is —$CH_2CH_3$;

$R_1$ is —$NH_2$, $R_2$ is —OH, $R_3$ is —CO(p-$C_6H_4$)$_3$O($CH_2$)$_4CH_3$, and $R_4$ is —$CH_2CH_2CH_2NH_2$;

$R_1$ is —$NH_2$, $R_2$ is —OH, $R_3$ is —CO(p-$C_6H_4$)$_3$O($CH_2$)$_4CH_3$, and $R_4$ is —$CH_2(CH_2)_3NH_2$;

$R_1$ is —$NH_2$, $R_2$ is —OH, $R_3$ is —CO(p-$C_6H_4$)$_3$O($CH_2$)$_4CH_3$, and $R_4$ is —$CH_2NH_2$;

$R_1$ is —$NH_2$, $R_2$ is —OH, $R_3$ is —CO(p-$C_6H_4$)$_3$O($CH_2$)$_4CH_3$, and $R_4$ is -2-(p-hydroxy-phenyl)ethyl;

$R_1$ is —$NH_2$, $R_2$ is —OH, $R_3$ is —CO(p-$C_6H_4$)$_3$O($CH_2$)$_4CH_3$, and $R_4$ is -3-guanidinopropyl;

$R_1$ is —$NH_2$, $R_2$ is —OH, $R_3$ is —CO(p-$C_6H_4$)$_3$O($CH_2$)$_4CH_3$, and $R_4$ is —H;

$R_1$ is —$NH_2$, $R_2$ is —F, $R_3$ is —CO(p-$C_6H_4$)$_3$O($CH_2$)$_4CH_3$, and $R_4$ is —CH(OH)$CH_3$;

$R_1$ is —$NHCH_3$, $R_2$ is —OH, $R_3$ is CO(p-$C_6H_4$)$_3$O($CH_2$)$_4CH_3$, and $R_4$ is —CH(OH)$CH_3$;

$R_1$ is —N($CH_3$)$_2$, $R_2$ is —OH, $R_3$ is CO(p-$C_6H_4$)$_3$O($CH_2$)$_4CH_3$, and $R_4$ is —CH(OH)$CH_3$;

$R_1$ is —$NHCH_2(C_6H_5)$, $R_2$ is —OH, $R_3$ is CO(p-$C_6H_4$)$_3$O($CH_2$)$_4CH_3$, and $R_4$ is —CH(OH)$CH_3$;

$R_1$ is —$NHCH_2$(p-$C_6H_4$)O$CH_2$COOH, $R_2$ is —OH, $R_3$ is CO(p-$C_6H_4$)$_3$O($CH_2$)$_4CH_3$, and $R_4$ is —CH(OH)$CH_3$;

$R_1$ is —$NHCH_2$(4-Pyridinyl) $R_2$ is —OH, $R_3$ is CO(p-$C_6H_4$)$_3$O($CH_2$)$_4CH_3$, and $R_4$ is —CH(OH)$CH_3$;

$R_1$ is —$NHCH_2COOH$, $R_2$ is —OH, $R_3$ is CO(p-$C_6H_4$)$_3$O($CH_2$)$_4CH_3$, and $R_4$ is —CH(OH)$CH_3$;

$R_1$ is —$NHCOCH_2CH_3$, $R_2$ is —OH, $R_3$ is CO(p-$C_6H_4$)$_3$O($CH_2$)$_4CH_3$, and $R_4$ is —CH(OH)$CH_3$;

$R_1$ is —$NHCOCH_3$, $R_2$ is —OH, $R_3$ is CO(p-$C_6H_4$)$_3$O($CH_2$)$_4CH_3$, and $R_4$ is —CH(OH)$CH_3$;

$R_1$ is —$NHCOC_6H_5$, $R_2$ is —OH, $R_3$ is CO(p-$C_6H_4$)$_3$O($CH_2$)$_4CH_3$, and $R_4$ is —CH(OH)$CH_3$;

$R_1$ is —NHCO(2-furoyl), $R_2$ is —OH, $R_3$ is CO(p-$C_6H_4$)$_3$O($CH_2$)$_4CH_3$, and $R_4$ is —CH(OH)$CH_3$;

$R_1$ is —NHCO(2-thienyl), $R_2$ is —OH, $R_3$ is CO(p-$C_6H_4$)$_3$O($CH_2$)$_4CH_3$, and $R_4$ is —CH(OH)$CH_3$;

$R_1$ is —NHCO(4-pyridinyl), $R_2$ is —OH, $R_3$ is CO(p-$C_6H_4$)$_3$O($CH_2$)$_4CH_3$, and $R_4$ is —CH(OH)$CH_3$;

$R_1$ is —NHCO(4-piperidinyl), $R_2$ is —OH, $R_3$ is CO(p-$C_6H_4$)$_3$O($CH_2$)$_4CH_3$, and $R_4$ is —CH(OH)$CH_3$;

$R_1$ is —NHCO(2-tetrahydrofuroyl), $R_2$ is —OH, $R_3$ is CO(p-$C_6H_4$)$_3$O($CH_2$)$_4CH_3$, and $R_4$ is —CH(OH)$CH_3$;

$R_1$ is —$NHCOOCH_3$, $R_2$ is —OH, $R_3$ is CO(p-$C_6H_4$)$_3$O($CH_2$)$_4CH_3$, and $R_4$ is —CH(OH)$CH_3$;

$R_1$ is —$NHCOCH_2CH=CH_2$, $R_2$ is —OH, $R_3$ is CO(p-$C_6H_4$)$_3$O($CH_2$)$_4CH_3$, and $R_4$ is —CH(OH)$CH_3$;

$R_1$ is —$NHCOCH_3$, $R_2$ is —OH, $R_3$ is CO(p-$C_6H_4$)$_3$O($CH_2$)$_4CH_3$, and $R_4$ is —CH(OH)$CH_3$;

$R_1$ is —$NHCONHN(CH_3)_2$, $R_2$ is —OH, $R_3$ is CO(p-$C_6H_4$)$_3$O($CH_2$)$_4CH_3$, and $R_4$ is —CH(OH)$CH_3$;

$R_1$ is —$NHCONHCH_2CH_2N(CH_3)_2$, $R_2$ is —OH, $R_3$ is CO(p-$C_6H_4$)$_3$O($CH_2$)$_4CH_3$, and $R_4$ —CH(OH)CH3;

$R_1$ is —$NHCH_2CH(NH_2)CH_2OH$, $R_2$ is —OH, $R_3$ is CO(p-$C_6H_4$)$_3$O($CH_2$)$_4CH_3$, and $R_4$ is —CH(OH)$CH_3$;

$R_1$ is —NHCO($CH_2$)$_2$COOH, $R_2$ is —OH, $R_3$ is CO(p-$C_6H_4$)$_3$O($CH_2$)$_4CH_3$, and $R_4$ is —CH(OH)$CH_3$;

$R_1$ is —$NHCOCH(NH_2)CH_2OH$, $R_2$ is —OH, $R_3$ is CO(p-$C_6H_4$)$_3$O($CH_2$)$_4CH_3$, and $R_4$ is —CH(OH)$CH_3$;

$R_1$ is —NHC=(NH)$NH_2$, $R_2$ is —OH, $R_3$ is CO(p-$C_6H_4$)$_3$O($CH_2$)$_4CH_3$, and $R_4$ is —CH(OH)$CH_3$;

$R_1$ is —$NHCOCH_2NH_2$, $R_2$ is —OH, R3 is CO(p-$C_6H_4$)$_3$O($CH_2$)$_4CH_3$, and $R_4$ is —CH(OH)$CH_3$;

$R_1$ is —$NHCOCH_2N(CH_3)_2$, $R_2$ is —OH, $R_3$ is CO(p-$C_6H_4$)$_3$O($CH_2$)$_4CH_3$, and $R_4$ is —CH(OH)$CH_3$;

$R_1$ is —$NHCOCH_2N^+(CH_3)_3$, $R_2$ is —OH, $R_3$ is CO(p-$C_6H_4$)$_3$O($CH_2$)$_4CH_3$, and $R_4$ is —CH(OH)$CH_3$; or $R_1$ is —$NH_2$, $R_2$ is —H, $R_3$ is —CO(p-$C_6H_4$)$_3$O($CH_2$)$4CH_3$, and $R_4$ is —CH(OH)$CH_3$.

9. A pharmaceutical composition comprising a compound according to claim 1 in combination with a pharmaceutically acceptable carrier.

10. A pharmaceutical composition comprising a compound according to claim 1 in combination with a pharmaceutically acceptable carrier.

11. A pharmaceutical composition comprising a compound according to claim 2 in combination with a pharmaceutically acceptable carrier.

12. A method of treating a fungal infection in a human or a veterinary patient comprising administering to the patient a therapeutically effective amount of a compound according to claim 1.

13. A method of treating a fungal infection in a human or a veterinary patient comprising administering to the patient a therapeutically effective amount of a compound according to claim 8.

14. A compound according to claim 8, wherein:

$R_1$ is —$NH_2$, $R_2$ is —OH, $R_3$ is —CO(p-$C_6H_4$)(Piperazinyl)($CH_2$)$_7CH_3$, $R_4$ is —CH(OH)$CH_3$;

$R_1$ is —$NH_2$, $R_2$ is —OH, $R_3$ is —CO(p-$C_6H_4$)(Piperazinyl)(p-$C_6H_4$)O—($CH_2$)$_7CH_3$, $R_4$ is —CH(OH)$CH_3$;

$R_1$ is —$NH_2$, $R_2$ is —OH, $R_3$ is —CO(p-$C_6H_4$)(Piperazinyl)(p-$C_6H_4$)O$CH_3$, $R_4$ is —CH(OH)$CH_3$;

$R_1$ is —$NH_2$, $R_2$ is —OH, $R_3$ is —CO(p-$C_6H_4$)(Piperazinyl)(p-$C_6H_4$)O—($CH_2$)$_4CH_3$, $R_4$ is —CH(OH)$CH_3$;

$R_1$ is —$NH_2$, $R_2$ is —OH, $R_3$ is —COO(p-$C_6H_4$)O—($CH_2$)$_7CH_3$, $R_4$ is —CH(OH)$CH_3$;

$R_1$ is —$NH_2$, $R_2$ is —OH, $R_3$ is —CO(p-$C_6H_4$)O—($CH_2$)$_7CH_3$, $R_4$ is —CH(OH)$CH_3$;

$R_1$ is —$NH_2$, $R_2$ is —OH, $R_3$ is —$CH_2$(p-$C_6H_4$)O—($CH_2$)$_7CH_3$, $R_4$ is —CH(OH)$CH_3$;

$R_1$ is —$NH_2$, $R_2$ is —OH, $R_3$ is CO(Piperazinyl)(p-$C_6H_4$)(p-$C_6H_4$)OCH$_3$, $R_4$ is —CH(OH)CH$_3$; or $R_1$ is —$NH_2$, $R_2$ is —OH, $R_3$ is CH$_2$(p-$C_6H_4$)(p-$C_6H_4$)O(CH$_2$)$_4$CH$_3$, $R_4$ is —CH(OH)CH$_3$.

15. A compound according to claim 1, wherein $R_7$ is selected from the group consisting of 4-alkoxyphenyl, 4-(alkylpiperazinyl)phenyl, 4-(4-(4'-alkoxyphenyl)-piperazinyl)phenyl, 4-((4'-alkoxy-(biphenyl))piperazinyl, 4'-((4-alkylpiperazinyl))-biphenyl, and 4-(4'-alkoxyphenyl)phenyl.

16. A compound according to claim 15, wherein $R_3$ is selected from the group consisting of —CH$_2$(p-C$_6$H$_4$)$_3$O(CH$_2$)$_4$CH$_3$, —CH$_2$p-C$_6$H$_4$O(CH$_2$)$_7$CH$_3$, —COO(p-C$_6$H$_4$)O(CH$_2$)$_7$CH$_3$, —CO(p-C$_6$H$_4$)O(CH$_2$)$_7$CH$_3$, —CO(p-C$_6$H$_4$)(Piperazinyl)(p-C$_6$H$_4$)O(CH$_2$)$_4$CH$_3$, —CO(p-C$_6$H$_4$)(Piperazinyl)-(p-C$_6$H$_4$)O(CH$_2$)$_7$CH$_4$, and —CO(p-C$_6$H$_4$)(Piperazinyl)(CH$_2$)$_7$CH$_3$.

* * * * *

UNITED STATES PATENT AND TRADEMARK OFFICE
CERTIFICATE OF CORRECTION

PATENT NO. : 5,696,084
DATED : December 9, 1997
INVENTOR(S) : Lartey, et al.

It is certified that error appears in the above-indentified patent and that said Letters Patent is hereby corrected as shown below:

Title page, in the title, please change "LIPOPETIDE", to --LIPOPEPTIDE--

Column 34, line 38, please delete
"10. A pharmaceutical composition comprising a compound according to claim 1 in combination with a pharmaceutically acceptable carrier."

Claims 11-16 should be renumbered to read claims 10-15.

Column 36, claim 15, "claim 15" should read -- claim 14 --.

Signed and Sealed this

Nineteenth Day of May, 1998

Attest:

BRUCE LEHMAN

Attesting Officer

Commissioner of Patents and Trademarks